United States Patent [19]
Starkweather

[11] Patent Number: 4,816,244
[45] Date of Patent: Mar. 28, 1989

[54] STABILIZED STAIN SOLUTIONS CONTAINING ALIPHATIC AND AROMATIC ALCOHOLS

[75] Inventor: William H. Starkweather, Keedysville, Md.

[73] Assignee: Sigma Chemical Company, St. Louis, Mo.

[21] Appl. No.: 829,200

[22] Filed: Feb. 14, 1986

[51] Int. Cl.$^4$ .................... A61K 31/60; G01M 1/30; G01M 31/00; G01M 33/48
[52] U.S. Cl. .......................................... 424/3; 8/435; 8/611; 514/166
[58] Field of Search ................ 424/3; 514/166; 8/435, 8/611

[56] References Cited

U.S. PATENT DOCUMENTS 3,670,072 6/1972 Mauthner .
4,363,632 12/1982 Custard .

OTHER PUBLICATIONS

Trotman, E. R., Dyeing and Chemical Technology of Textile Fibres, John Wiley & Sons (New York, 1984), p. 350.
Mellan, I. Industrial Solvents, Reinhold Publ. Corp., (New York, 1950), pp. 482–483, 503, 507, 511.

Primary Examiner—Stanley J. Friedman
Attorney, Agent, or Firm—Arthur S. Morgenstern

[57] ABSTRACT

Medium molecular weight alcohols (for example aliphatic alcohols, such as trihydroxypentane and trihydroxyhexane, and aromatic alcohols, such as benzylalcohol) have been found to provide unexpected stability to dye and stain solutions. In addition, the use of these alcohols does not involve the negatives found in other dye stabilizers, for example extreme flammability and toxicity. The novel alcohols have been found to provide benefit to many dye systems.

2 Claims, No Drawings

STABILIZED STAIN SOLUTIONS CONTAINING ALIPHATIC AND AROMATIC ALCOHOLS

BACKGROUND OF THE INVENTION

Dyes and stain solutions have been used for years, and many of the formulations have not been improved since their initial development. This is particularly true for biological dyes and stain solutions which are used to study plant and animal tissues. One of the problems often encountered with biological stains and dyes regards their stability in solution. In many formulations dye instability is due to variability of the dye components. In other cases, the instability is due to the solvent system.

There has been much interest in recent years in Wright Stains (Romanowsky Stains). In addition to having recently understood the chemical composition of this stain system, workers have attempted to stabilize the system (i.e., prevent the active ingredients from precipitating from solution) by using various approaches. One approach was to use low molecular weight alcohols (eg, methanol, ethanol) and glycerols to solubilize the dye solids and keep them in solution. However, these solvents tend to promote the oxidation of the dyes, which in turn leads to less soluble decomposition products and resulting solution deterioration. Other solvents used have included glycerol, propylene glycol and ethylene glycol monomethyl ether. Many of these solvents are extremely hazardous (i.e., flammable, extremely toxic and possibly teratogenic). As a result, there are many negative aspects involved with using these materials. In addition, although they may stabilize the system to some extent, they fall short in providing the needed stability for a commercially feasible, long shelf life system. The current invention eliminates all of the above problems, and it has been found to provide the needed benefits for Romanowsky and a number of other dye and stain systems.

SUMMARY OF THE INVENTION

The current invention involves the use of a novel solvent, either trihydroxy hexane, benzyl alcohol, another moderate molecular weight alcohol, or a combination of these solvents, in dye and stain solutions in order to provide much improved stability over previously formulated systems. In addition, these alcohols do not exhibit many of the negative attributes found with other stabilizers.

DESCRIPTION OF THE INVENTION

The use of trihydroxyhexane or other water soluble or miscible moderate weight alcohols containing 4-8 carbons (eg., trihydroxypentane and benzyl alcohol) or a combination . . . earlier used ingredients. These stabilizing alcohols should be used at 2-70% concentration to achieve the desired benefit. Previously, workers had attempted to use ethylene glycol, ethylene glycol monomethyl ether, diethylene glycol, propylene glycol, ethanol and propanol but found not benefit from these solvents in Wright stain and related systems. Limited success was achieved by using approximately 20% glycerol in Wright stain. However, in order for the glycerol to be effective, it was necessary for workers to first, dilute the system prior to use, and second, employ prefixed blood films. Both of these are inconvenient and non-routine for the laboratory technologist. The novel alcohols provide much improved stability vs. the chemicals used by other workers in the dye and stain area. In addition, they have been found to provide low temperature stability and to prevent precipitation when small quantities of water are inadvertently added to the systems (eg, due to absorption from the atmosphere). Furthermore, it has been found that these alcohols inhibit the oxidation that often occurs in the dye components themselves.

These newly used alcohols have been evaluated in various types of dyes, including xanthine type dyes (for example, Eosin Y), thiazine dye systems (for example, methylene blue and Azure A, B, and C), natural dyes (eg, hematoxylin), diazo and polyazo dyes (eg, Sudan Black B), and aminiotriaryl . . . (eg, pararosaniline). The concentration of dyes and stains found to benefit by the stabilizing alcohols range from 0.01-10.0%. The alcohols stability in systems composed of mixtures of these dyes. Due to the variety of dye systems in which they have been found to improve stability it is believed that these alcohols should be considered for stability purposes when workers are formulating any dye system.

EXAMPLE 1

A Wright Stain (Romanowsky Stain) was formulated, comprised of Azure B 0.15%, and Eosin Y, 0.15%. These ingredients were added to 800-900 ml absolute methanol, and the system was thoroughly mixed for twenty minutes. Trihydroxyhexane (10-20%) was then added and mixed for another ½ hour. The resulting solution was compared for stability versus a system where glycerol had been used instead of the trihydroxyhexane. The system containing trihydroxyhexane was found to be more stable to low temperature and found to have less precipitation of dye component.

EXAMPLE 2

Azure B (1 ½ grams) and Eosin Y (1 ½ grams) were dissolved in 750 ml methanol solution and mixed for 20 minutes. Trihydroxyhexane (250 ml) was added and stirred for 30 minutes. This solution was found stable in freezer storage and no precipitation of dye components was found.

EXAMPLE 3

Sudan Black B was dissolved in a dilute ethanol solution buffered with phosphate and trihydroxyhexane. (Sudan Black B concentration was equal to 0.18%, phosphate 0.35%, trihydroxyhexane 5%, alcohol 60%, balance water). The stability of this system was found to be much improved versus that containing phenol instead of trihydroxyhexane.

EXAMPLE 4

Hematoxylin (7.5%) was dissolved in water along with aluminum ammonium sulfate (22%) and sodium iodate (0.75%) The solution was mixed for 30 minutes and allowed to set overnight. All undissolved components were then filtered out and trihydroxyhexane (15% of final concentration) was then added and mixed for 30 minutes. This solution was compared to a similar one in which trihydroxyhexane was replaced with glycerol or diethylene glycol. The trihydroxyhexane solution was found to be more easily prepared, was filtered more readily and provided much improved stability.

EXAMPLE 5

Aluminum ammonium sulfate (22 grams) was dissolved in 1 liter of water, and 7.5 grams of hematoxylin was then added and dissolved. Sodium iodate (0.75 grams) was then added to oxidize the hematoxylin. The solution was checked on a spectrophotometer at 560 mu, and additional water was added until the absorbance reached 0.325. At that point, 150 ml of trihydroxyhexane was added. The resulting solution was found much improved in stability versus the previously formulated systems.

EXAMPLE 6

Pararosaniline (basic fuchsin), 25 grams, was dissolve in 120 ml of methanol. The solution was then filled to 940 ml with deionized water. Trihydroxy hexane (600 milliliters) was then added. This solution was found much improved in stability versus the solution where phenol had been used instead of trihydroxyhexane.

The foregoing examples are merely illustrative of the present invention.

What is claimed is:

1. A stabilized biological dye or stain solution wherein the stabilizer system comprises from 2 to 70% of a compound selected from the group trihydroxyhexane, trihydroxypentane, and benzyl alcohol, and the dye or strain comprises components selected from the group:
   a. Eosin Y,
   b. methylene blue, Azure A, Azure B, Azure C, or a combination of two or more of these components,
   c. hematoxylin,
   d. Sudan Black B, and
   e. pararosaniline.

2. A biological dye or stain solution comprising 0.15% Azure B, 0.15% Eosin Y, 10-30% trihydroxyhexane, and up to 90% methanol.

* * * * *

UNITED STATES PATENT AND TRADEMARK OFFICE
CERTIFICATE OF CORRECTION

PATENT NO. : 4,816,244

DATED : March 28, 1989

INVENTOR(S) : William H. Starkweather

It is certified that error appears in the above-identified patent and that said Letters Patent is hereby corrected as shown below:

Column 1, line 60, delete "not" and insert --no--.
Column 2, line 15, delete "aminiotriaryl...." and insert --aminotriarylmethane dyes --.
Column 4, line 10, delete "strain" and insert --stain--.

Signed and Sealed this

Fifth Day of June, 1990

Attest:

HARRY F. MANBECK, JR.

*Attesting Officer*     *Commissioner of Patents and Trademarks*